United States Patent
Riesenberg et al.

(10) Patent No.: US 6,416,785 B1
(45) Date of Patent: Jul. 9, 2002

(54) MOLECULAR PROBES FOR TARGETING OF CELL DENSITY-INDICATING COMPOUNDS

(75) Inventors: Dieter Riesenberg, Jena; Volker Schroeckh, Rothenstein; Burkhard Gitter, Jena, all of (DE); Wolfgang Neuberger, Labuan (MY)

(73) Assignee: Biolitec AG, Jena (DE)

( * ) Notice: Subject to any disclaimer, the term of this patent is extended or adjusted under 35 U.S.C. 154(b) by 0 days.

(21) Appl. No.: 09/644,952

(22) Filed: Aug. 23, 2000

(51) Int. Cl.⁷ .................. A61K 9/127; A61K 38/62; A61K 38/16; A61K 39/395
(52) U.S. Cl. .................. 424/450; 514/2; 514/6; 424/178.1; 424/630; 424/646; 424/179.1; 424/186.1; 424/181.1
(58) Field of Search .................. 514/1, 2, 6; 435/7.1, 435/7.32; 424/450, 178.1, 630, 646, 179.1, 180.1, 181.1; 530/350, 389.5

(56) References Cited

FOREIGN PATENT DOCUMENTS

| WO | WO 98/57618 | 12/1998 |
|----|-------------|---------|
| WO | WO 99/27786 | 6/1999  |
| WO | WO 00/32152 | 6/2000  |

OTHER PUBLICATIONS

Zhu et al. Proceedings of the National Academy of Sciences USA 96:4832–4837, 1999.*
Balaban et al. Science 280:438–440, Apr. 17, 1998.*
Wainwright M. "Photodynamic antimicrobial chemotherapy (PACT)" J. Antimicrobial Chemotherapy, 42: 13–28 (1998).
Dunny G.W. and Winans S.C. "Cell–cell signaling in bacteria" ASM, Washington D.C. (1999).
England R. et al., "Microbial signaling and communication" Symposium 57 of the General Microbiology, Cambridge University Press, (1999).
Bassler B.L. "How bacteria talk to each other: regulation of gene expression by quorum sensing" Current Opinion in Microbiology, 2: 582–587 (1999).
Jansen J. et al., "Encapsulation of guest molecules into a dendritic box" Science, 266:1226–1229 (1994).

* cited by examiner

*Primary Examiner*—Mary E. Mosher
(74) *Attorney, Agent, or Firm*—BJ Associates; Bolesh J. Skutnik

(57) ABSTRACT

A new approach for targeting chemotherapeutics to focal bacterial infections is provided. Such focal infections are characterized by high densities of different bacteria and thus high concentrations of their extracellular signal molecules sensing the cell density. In gram-negative bacteria, one of such signal molecules is acyl-homoserine lactone (acyl-HSL, member of the autoinducer family AI-1), wherein species-specificity is achieved by acyl-residues, and HSLs are common for all gram-negative bacteria. In gram-positive bacteria, oligopeptides secreted by the bacteria communicate the cell density. In addition, there are cell density signal molecules (members of the autoinducer family AI-2) which communicate between gram-positive and gram-negative bacteria. The general scheme of the present invention is molecular modules that comprise both a targeting component and a chemotherapeutical component which serves for photodynamic antimicrobial chemotherapy (PACT). One preferred embodiment of the present invention is to target photosensitizers to the extracellular signal molecules instead of on the bacteria themselves. Targeting of the photosensitizers is mediated via molecules with efficient binding to the HSL-moiety of the acyl-HSL, so that a broad spectrum of gram-negative bacteria can be knocked out. Photosensitizers used in the present invention can be packed into special liposomes with lipid chelators or multiple coupled to dendrimers, so that they are especially effective for PACT. In addition, selected molecules with high affinity to a common moiety of such signal molecules, like HSL, may be used as molecular probes for the search of yet undiscovered cell density dependent signals.

7 Claims, 1 Drawing Sheet

MOLECULAR PROBES FOR TARGETING OF CELL DENSITY-INDICATING COMPOUNDS

BACKGROUND OF THE INVENTION

1. Field of the Invention

The present invention relates generally to photodynamic antimicrobial chemotherapy (PACT) and in particular to molecules which are capable of identification and targeting of cell density-indicating compounds secreted by bacteria.

2. Invention Disclosure Statement

Bacteria infection or contamination has been a problem in different areas, and various methods have attempted to solve the problem. A major breakthrough is the discovery and later synthesis of antibiotics. However, most antibiotics have a limited anti-bacterial spectrum, and varieties of bacterial strain have been found antibiotic-resistant. Moreover, certain antibiotics have serious side effects when administered systemically, especially in the treatment of focal infections because a large dosage has to be given for the drug to reach the therapeutic concentration in the infected area. Scientists have long been trying to find new methods to treat bacteria infections more effectively and with fewer side effects.

Photodynamic antimicrobial chemotherapy (PACT) is one of the technologies developed in recently years. Wainwright M, *Photodynamic antimicrobial chemotherapy (PACT)*, J. Antimicrobial Chemotherapy, 42: 13–28 (1998) discloses the PACT-technology utilizing photosensitizers, which is effective against bacteria, yeast, virus, and parasites in vitro. It is thought that delivering energy (e.g. radiation) to a photosensitizer (such as chlorin compound, or phthalocyanine) results in the formation of singlet oxygen which is a highly reactive form of oxygen. Singlet oxygen functions as a toxic agent that kills bacterial cells. This technique is often used for sterilization of blood preparations. However, since singlet oxygen also harms normal cells, the PACT-technology is mainly restricted to local dental treatment in vivo.

Another attempt has been focused on the destruction of biofilms. Biofilms are biological films which are produced by the bacteria. Since biofilms can trap nutrients and also play an important role in cell-cell communication between bacterial cells, destruction of biofilms may prevent or treat bacterial infections. Both WO 99/27786 and WO 98/57618 disclosed compounds that can control biofilm formation.

Dunny G W and Winans S C, *Cell-cell signaling in bacteria*, ASM Wash. D.C. (1999) and England R et al., *Microbial signaling and communication*, Symposium 57 of the General Microbiology, Cambridge University Press, (1999) have shown the cell-cell communication system from several unicellular bacteria. The cell-cell communications are both intraspecies-specific and interspecies-specific. Such communication system comprises molecules which are called autoinducers or quorum sensors. Gram-negative bacteria (e.g. Vibrio, Pseudomonas, or Yersinia) accumulate acyl-homoserine lactones (acyl-HSL) in the bacterial cells and in their surroundings, such as nutrient medium or biofilms. In acyl-HSL, the moiety HSL is common for all gram-negative bacteria, whereas the species-specificity is given by the various acyl residues. Bassler B L, *How bacteria talk to each other: regulation of gene expression by quorum sensing*, Current Opinion in Microbiology, 2: 582–587, (1999) demonstrates HSL with various acyl-chains can be considered as members of cell density sensor (or autoinducer AI-1) family of gram-negative bacteria. In different species, the acyl residues have different characteristics, such as different length, and different degree of saturation in their C—C bonds. Acyl-HSL can activate several molecular pathways in bacteria when a significant population of cells has accumulated, and the activation leads to species-specific responses (e.g. virulence, formation of antimicrobial immune modulating compounds). This type of regulation is named "quorum sensing" because the activation is cell-density dependent. Quorum sensing is critical in biofilm formation, and both WO 99/27786 and WO 98/57618 utilized such characteristics of HSL to provide compounds, which block the quorum sensing and thus prevent biofilm formation.

Acyl-HSL is identified by various biosensor tests and chemical standard methods. Biosensors usually detect bacteria cells directly. Using a probe for identification of HSL as common moiety of all acyl-HSL has not yet been described. Gamma-butyrolactones are signal molecules which control the secondary metabolism in Streptomyces species. Novick R P and Muir T W, *Virulence gene regulation by peptides in staphylococci and other gram-positive bacteria*, Current Opinion in Microbiology, 2: 40–45 (1999) show gram-positive bacteria (e.g. Streptococcus, Staphylococcus) communicate their cell density via extracellular peptides. These peptides are species-specific. Group specific domains of the various cell density indicating peptides (like HSL in acyl-HSL) are not known so far. Recently, WO 00/32152 discloses a new autoinducer, AI-2 or 4,5-Dihydroxy-2,3-pentanedione, which communicates interspecies-specific signals between gram-negative and gram-positive bacteria. AI-2 cell density sensor probably belongs to a new family of cell density sensors since WO 00/32152 shows that the various OH-groups in 4,5-Dihydroxy-2,3-pentanedoine may be replaced by other residues in other bacteria.

A possibility for increasing the concentration of photosensitizers accumulated in areas of focal bacterial infections is the use of dendrimers as multiplier molecules. Jansen J et al., *Encapsulation of Guest Molecules into a Dendritic Box*, Science, 266: 1226–1229, (1994) demonstrate that dendrimers are molecules for guest host embedding. Dendrimers are also molecules for multiple covalent coupling of photosensitizers to the periphery of the dendrimer.

Attempts also have been made to minimize side effects of antimicrobial compounds, such as photosensitizers, by linking them to monoclonal antibodies which directly bind on the surface of pathogenic bacteria. This method seems to be not economical for several reasons: first, it is costly to raise monoclonal antibodies; second, fast mutation rate of variety of bacteria require different monoclonal antibodies for different strains as well as for different mutants. Moreover, the usually large quantity of bacteria infected increases the dosage requirement of the drug.

It is well known that a focal disease is characterized by high concentration of bacteria, and hence by a high extracellular concentration of the cell-density sensing molecules, such as acyl-HSLs, peptides, which surround the bacteria. However, molecular modules comprising at least of two molecular parts, one with binding affinity to cell-density signals (i.e. HSL, peptide) and another being a therapeutic compound such as photosensitizers, have never been shown. The present invention describes such molecular modules that can be used for targeting of photosensitizers into focal diseases. In addition, molecules with binding affinity to HSL may serve as probes for detection of new acyl-HSLs as the cell density signals.

BRIEF SUMMARY AND OBJECTS OF THE INVENTION

It is an object of the present invention to provide molecular modules that are capable of targeting antimicrobial chemotherapeutics to areas of focal bacterial infections.

It is another object of the present invention to target antimicrobial chemotherapeutics to extracellular signal molecules synthesized by bacteria instead of bacterial cell surfaces.

Yet another object of the present invention is to provide molecular modules capable of binding to HSL, the common moiety of all acyl-HSLs (AI-1 family members), so that it will lead to inactivation of a broad spectrum of gram-negative bacteria.

It is a further object of the present invention to provide molecular modules targeting chemotherapeutics to species-specific peptides secreted by gram-positive bacteria.

It is a further object of the present invention to provide molecular probes targeting chemotherapeutics to cell density sensors of both gram-negative and gram-positive bacteria (AI-2 family members), so that it will be lead to inactivation (inhibition) of a broad spectrum of gram-negative and gram-positive bacteria.

Briefly stated the present invention provides a new approach for targeting chemotherapeutics to focal bacterial infections. Such focal infections are characterized by high densities of different bacteria and thus high concentrations of their extracellular signal molecules sensing the cell density. In gram-negative bacteria, one of such signal molecules is acyl-homoserine lactone (acyl-HSL, member of the autoinducer family AI-1), wherein species-specificity is achieved by acyl-residues, and HSLs are common for all gram-negative bacteria. In gram-positive bacteria, oligopeptides secreted by the bacteria communicate the cell density. In addition, there are cell density signal molecules (members of the autoinducer family AI-2) which communicate between gram-positive and gram-negative bacteria. The general scheme of the present invention is molecular modules that comprise both a targeting component and a chemotherapeutical component which serves for photodynamic antimicrobial chemotherapy (PACT). One preferred embodiment of the present invention is to target photosensitizers to the extracellular signal molecules instead of on the bacteria themselves. Targeting of the photosensitizers is mediated via molecules with efficient binding to the HSL-moiety of the acyl-HSL, so that a broad spectrum of gram-negative bacteria can be knocked out. Photosensitizers used in the present invention can be packed into special liposomes with lipid chelators or multiple coupled to dendrimers, so that they are especially effective for PACT. In addition, selected molecules with high affinity to a common moiety of such signal molecules, like HSL, may be used as molecular probes for the search of yet undiscovered cell density dependent signals.

The above, and other objects, features and advantages of the present invention will become apparent from the following description read in conjunction with the accompanying drawings.

DETAILED DESCRIPTION OF PREFERRED EMBODIMENTS

Figure 1:
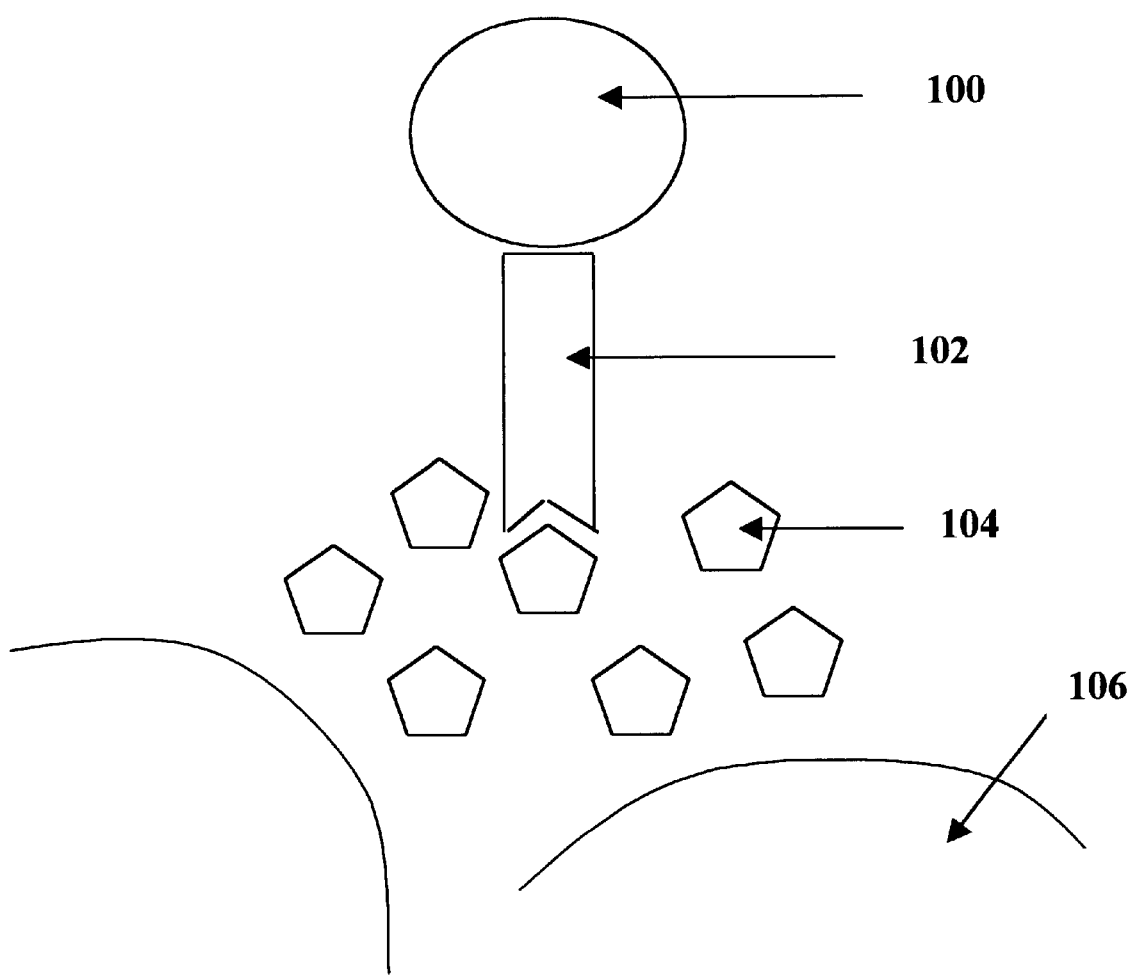
FIG. 1 shoes the general scheme of the present invention.

The present invention describes molecular modules that target antimicrobial chemotherapeutics to focal bacterial infections. Instead of directly targeting bacteria cells, the present invention targets cell communication signal molecules secreted by the bacteria. Gram-negative bacteria secrete acyl-HSLs to their surroundings as sensors to detect the cell density. The moiety HSL is common for all gram-negative bacteria, while the species-specificity is achieved by various acyl residues. In different species, the acyl residues have different characteristics, such as different length, and different degree of saturation in their C—C bonds. Gram-positive bacteria communicate their cell density via extracellular peptides. These peptides are species-specific. Compounds of the AI-2 family are interspecies-specific. Molecular modules provided by the present invention comprise a molecular component with binding affinity to cell density sensing molecules (such as acyl-HSL in gram-negative bacteria, or peptides in gram-positive bacteria), and a molecular component representing an antimicrobial drug (such as antibiotics, photosensitizers). When the drug is a photosensitizer, it can be packed into special liposomes, where chelator lipids with copper or nickel head are incorporated, so that it is especially effective for photodynamic antimicrobial chemotherapy. For increasing the efficiency of PACT, the multiple coupling of the dye molecules to dendrimers is also possible. The antimicrobial drug can be linked directly or via linkers indirectly to the molecular component with binding affinity. For gram-negative bacteria, the molecular component with binding affinity to cell density sensing molecules can be peptides, respectively proteins.

The present invention provides certain advantages. First, when targeting the common moiety HSL of acyl-HSL secreted by gram-negative bacteria, and using a wide spectrum antimicrobial drug such as a photosensitizer, a broad spectrum of gram-negative bacteria will be killed, and the targeting will not be limited to certain gram-negative bacteria strains. Second, since most focal infections are a mix of gram-positive and gram-negative bacteria, the present invention provides a drug delivery system that concentrates drugs in the infected area while targeting several types of bacteria. Third, since this delivery system concentrates antimicrobial drugs in the infected area, it minimizes side effects of certain drugs. Furthermore, a molecular component with high affinity to a common moiety of a signal molecule, such as HSL, can be used as a probe for the search of yet undiscovered cell density dependent signals with species-specific residues, which provides valuable information for future research.

FIG. 1 shows the general scheme of the present invention. Antimicrobial drug 100 is linked to molecular component 102 either directly or indirectly through a linker. Molecular component 102 has high affinity to cell density sensing molecule 104, such as acyl-HSL in gram-negative bacteria or peptides in gram-positive bacteria. Therefore, antimicrobial drug 100 is concentrated at the infected area by targeting to cell density sensing molecule 104 instead of binding directly to bacterial cell 106.

Having described preferred embodiments of the invention with reference to the accompanying drawing, it is to be understood that the invention is not limited to the precise embodiments, and that various changes and modifications may be effected therein by skilled in the art without departing from the scope or spirit of the invention as defined in the appended claims.

What is claimed is:

1. An antibacterial composition, comprising at least one photosensitizer suitable for photodynamic antimicrobial therapy, linked to a polypeptide with binding affinity for an acyl-homoserine lactone, or for autoinducer AI-2.

2. The composition of claim 1, wherein the photosensitizer is packed in liposomes.

3. The composition of claim 1, wherein the photosensitizer is linked directly to the polypeptide.

4. The composition of claim 1, wherein the photosensitizer is linked indirectly by linkers to the polypeptide.

5. The composition of claim 2, wherein chelator lipids having heads selected from a group consisting of copper and nickel are incorporated into said liposomes, and said polypeptide with binding affinity is histidine-tagged.

6. The composition of claim 4, wherein said linkers are multiplier molecules.

7. The composition of claim 1, which can be applied to mixed populations of gram-negative and gram-positive bacteria.

* * * * *